United States Patent
Cunsolo et al.

(10) Patent No.: US 7,465,820 B2
(45) Date of Patent: Dec. 16, 2008

(54) ABIOTIC HEPARIN ANTAGONISTS

(75) Inventors: Francesca Cunsolo, Valverde (IT);
Grazia Maria Letizia Consoli, Valverde (IT); Corrada Geraci, Valverde (IT);
Tommaso Mecca, Valverde (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 52 days.

(21) Appl. No.: 10/572,387

(22) PCT Filed: Sep. 16, 2004

(86) PCT No.: PCT/EP2004/010358

§ 371 (c)(1),
(2), (4) Date: Mar. 16, 2006

(87) PCT Pub. No.: WO2005/028422

PCT Pub. Date: Mar. 31, 2005

(65) Prior Publication Data

US 2007/0082951 A1 Apr. 12, 2007

(30) Foreign Application Priority Data

Sep. 19, 2003 (IT) .......................... MI2003A1790

(51) Int. Cl.
*C07C 229/02* (2006.01)
*A61K 31/22* (2006.01)
*A61K 31/225* (2006.01)

(52) U.S. Cl. ...................... 560/138; 554/107; 514/548; 514/551

(58) Field of Classification Search ........................ None
See application file for complete search history.

(56) References Cited

U.S. PATENT DOCUMENTS 5,409,959 A 4/1995 Hwang et al.

OTHER PUBLICATIONS

Manabe (Chem. Abstract 1988:570,072, abstract of JP 62265250).*
Database Beilstein Beilstein Institut Zur Forderung Der Chemischen Wissenschaft, Frankfurt Am Main, DE; XP002317711 retrieved rom XFIRE Database accession No. 8824309, 8823238, 7679682 abstract & Eur. J. Org. Chem., vol. 3, 2001, pp. 595-602.
Database Beilstein Beilstein Institut Zur Forderung Der Chemischen Wissenschaft, Frankfurt Am Main, DE; XP002317712 retrieved from XFIRE Database accession No. 8246996, 8248224, 8247802, 8247910, 5201176 abstract & J. Prakt. Chem.-Ztg.,viol. 341, No. 3, 1999, pp. 264-273.
Database Beilstein Beilstein Institut Zur Forderung Der Chemischen Wissenschaft, Frankfurt Am Main, DE; XP002317713 retrieved from XFIRE Database accession No. 522504 abstract & J. Am. Chem Soc., vol. 111, No. 14, 1989, pp. 5477-5478.
Database Beilstein Beilstein Institut Zur Forderung Der Chemischen Wissenschaft, Frankfurt Am Main, DE; XP002317714 retrieved from XFIRE Database accession No. 7789075 abstract & J. Am. Chem. Soc., vol. 119, No. 24, 1997, pp. 5706-5712.
Database Beilstein Beilstein Institut Zur Forderung Der Chemischen Wissenschaft, Frankfurt Am Main, DE; XP002317715 retrieved from XFIRE Database accession No. 7563513 abstract & Angew. Chem., vol. 108, No. 12, 1996, pp. 1425-1427.
Database Beilstein Beilstein Institut Zur Forderung Der Chemischen Wissenschaft, Frankfurt Am Main, DE; XP002317716 retrieved from XFIRE Database accession No. 91109666 abstract & Org. Lett., vol. 4, No. 10, 2002, pp. 1687-1690.
Database Beilstein Beilstein Institut Zur Forderung Der Chemischen Wissenschaft, Frankfurt Am Main, DE; XP002317717 retrieved from XFIRE Database accession No. 9539937 abstra=ct & New J. Chem. vol. 26, No. 5, 2002, pp. 651-655.
Reeza Zadmard et al: "Capsule-like Assemblies in Polar Solvents" J. Org. Chem., vol. 68, No. 17, Jul. 24, 2003, pp. 6511-6521, XP002317709 p. 6515, fig. 7, compounds 17, 18.
Database Beilstein Beilstein Institut Zur Forderung Der Chemischen Wisenschaft, Frankfurt Am Main, DE; XP002317718 retrieved from XFIRE Database accession No. 5466493 abstract & J. Org. Chem., vol. 57, No. 13, 1992, pp. 3658-3662.
Database CAPLUS 'Online! Chemical Abstracts Service, Chemical Abstracts Service, Columbus, Ohio, US; Iwata, Kazunori et al Iwata, Kazunori et al: "Supports for adsorption chromatography Supports for adsorption chromatography" XP002317719 retrieved from STN Database accession No. 1994:338122 abstract & JP 05 264531 A2 (Showa Denko KK, Japna Showa Denko KK, Japan) Oct. 12, 1993.
Database CAPLUS 'Online! Chemical Abstracts Service, Columbus, Ohio US; Jakobi, Ralf A. et al: "Long-chain alkyl ethers of p-nitro- and p-aminocalixarenes" XP002317720 retrieved from STN Database accession No. 1996:287626 abstract & New Journal of Chemistry , 20(4), 493-501 coden: NJCHE5; ISSN: 1144-0546, 1996.
Tommasao Mecca et al: 'Design calix'8!arene-based ligands for selective tryptase surface recognition Bioorg. Med. Chem.M vol. 12, Aug. 20, 2004, pp. 5057-5062, xp002317710 p. 5061: compounds 2-6 and their trifluoroacetic salts.
Consoli G M L et al: "Calix'8!arene-based glycoconjugates as multivalent carbohydrate-presenting systems" Tetrahedron Letters, Elsevier Science Publishers, Amssterdam, NL, vol. 44, No. 40, Sep. 29, 2003, pp. 7467-7470, XP004453448 ISSN: 0040-4039 p. 7468, compound 1.

* cited by examiner

*Primary Examiner*—Samuel A Barts
(74) *Attorney, Agent, or Firm*—Young & Thompson

(57) ABSTRACT

The present invention relates to heparin-binding calixarene compounds of general Formula (I) in which R, $R_1$, L and n have the meanings indicated in the description and their use in the biomedical field.

13 Claims, No Drawings

ABIOTIC HEPARIN ANTAGONISTS

FIELD OF THE INVENTION

The present invention relates to heparin antagonists, in particular to protamine-mimetic compounds having a calixarene structure.

TECHNOLOGICAL BACKGROUND

Heparin, a sulfonated polysaccharide belonging to the glycosaminoglycans family, is a compound having anticoagulant activity due to its ability to increase the rate with which antithrombin inhibits serine-proteases involved in the blood coagulation cascade.[1-2]

Further to exerting anticoagulant action, heparin partecipates, together with its analogue heparan-sulfate, in several processes, such as cell growth, migration and differentiation. In fact it is involved, both in the free form and bound to proteins, in the angiogenesis and growth of tumoral tissues. [3-7]

Due to its anticoagulant action, heparin is widely used in post-surgical protocols for the prevention of thromboembolism, clotting and thrombi occurring after surgery interventions on the cardiocirculatory system. It is also used in procedures which envisage extracorporeal blood circulation, such as hemodialysis, in therapeutical protocols which involve the use of artificial organs and in organ transplants. In all these cases heparin effects and concentration have to be controlled, and sometimes neutralized, in order to avoid lethal haemorrhages. Therefore, molecules capable of inhibiting heparin or reduce its plasma concentration have interesting therapeutical applications.

At present protamine sulfate is the sole compound used systemically in the treatment of heparin overdosage. Protamine is a low molecular weight protein, extracted from the spermatic cells of some fish, characterized by the presence of a number of arginine residues which render it strongly basic. In a pH range ranging from 6 to 7 protamine, present in cationic form, neutralizes anionic heparin, forming an insoluble and inactive complex. However, sometimes protamine causes side effects, such as hypotension, bradycardia, thrombocytopenia, leucopenia, anaphylactic shock, etc.[8]

Despite continuos efforts to develop novel, more efficient dialysis membranes[9], anticoagulation and neutralization of any anticoagulant excess is still accomplished by heparin-protamine perfusion.

There is therefore the need for molecules that are safer than protamine, especially for extra corporeal devices useful for the prevention of clotting in dialysis circuits, and that allow to reduce to a minimum the risk of haemorrhage in dialysed patients.

It has recently been reported[10-12] that polyphenolic macrocyclic oligomers, commonly referred to as calixarens[12], can be used in the synthesis of polyfunctional mimetic antibodies (U.S. Pat. No. 5,770,380).

WO 01/70930 A2 discloses compounds having a calixaren structure, in particular calix[4]arenes capable of binding growth factors. In particular, each calixarene unit contains arylcarboxylate groups linked to one another at the ortho position to form a macrocycle. Moreover, each calixarene unit bears an alkoxy substituent at the para position to the carboxylic group, which imparts a rigid conformation. Peptidic loops, preferably hexapeptidic loops in which two aminoacids are replaced by a 3-amino-benzamido group, are linked to all or some of the carboxylic groups.

DISCLOSURE OF THE INVENTION

It has now been found that calixarenes substituted with amino acids bearing salifiable amino groups are heparin ligands more advantageous than protamine.

The present invention relates to heparin-binding calixarene compounds of general formula (I)

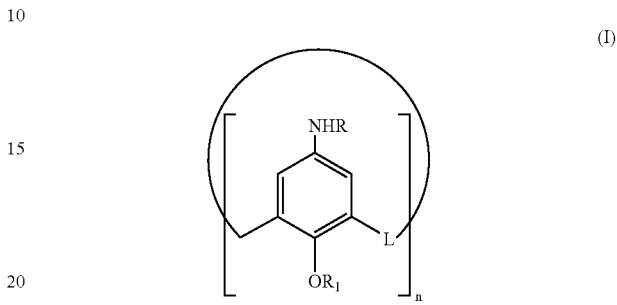

wherein:

groups R are independently hydrogen or an amino acid acyl residue;

$R_1$ is hydrogen, straight or branched $C_1$-$C_5$ alkyl, or benzyl;

L is selected from $CH_2$, $CH_2OCH_2$ or S;

n is an integer ranging from 4 to 12 and the salts thereof with physiologically compatible acids.

The term "amino acid" identifies a natural alpha-amino acid or a straight or branched aliphatic $C_2$-$C_8$ amino acid.

In the compounds of formula (I) the acyl residue is preferably the acyl residue of an amino acid selected from: lysine, β-alanine, γ-amino-butyric acid, 6-amino-hexanoic acid, 8-amino-octanoic acid, norleucine, glycine.

Moreover, in the compounds of formula (I), n is preferably 4 or 8, more preferably 8, L is preferably $CH_2$ and $R_1$ is preferably propyl.

A first group of preferred compounds of formula (I) is that in which:

groups R are independently hydrogen or the acyl residue of an amino acid selected from lysine, β-alanine, γ-amino-butyric acid, 6-amino-hexanoic acid, 8-amino-octanoic acid, norleucine and glycine;

$R_1$ is propyl;

L is $CH_2$;

n is 4.

A second group of preferred compounds of formula (I) is that in which:

groups R are independently hydrogen or the acyl residue of an amino acid selected from lysine, β-alanine, γ-amino-butyric acid, 6-amino-hexanoic acid, 8-amino-octanoic acid, norleucine e glycine;

$R_1$ is propyl;

L is $CH_2$;

n is 8.

In this second group, particularly preferred is the compound in which all the groups R are lysine acyl residues, namely compound (Ia):

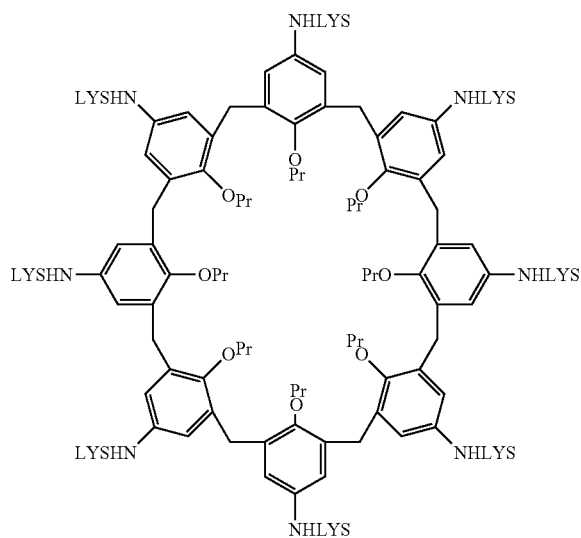

in which LYS represents lysine.

For the biological use of the compounds of formula (I), all or some of the amino groups in the R groups are salified with a physiologically compatible acid and present in the cationic form.

The term "physiologically compatible acid" identifies an inorganic or organic acid preferably selected from: hydrochloric, phosphoric, citric, sulfuric, lactic, acetic acid.

In general, the synthesis of the compounds of formula (I) comprises the alkylation of the phenolic hydroxyl of a calixarene of general formula (II)

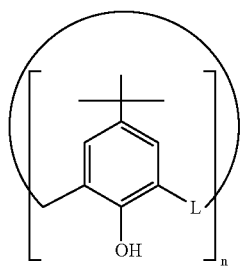

in which L and n are as defined above, with an alkyl halide $R_1X$, in which $R_1$ is as defined above, the nitration at the para position, with simultaneous substitution of the tert-butyl group, the reduction of the nitro group to amino group and the acylation with the selected amino acid.

The compounds of formula (I) and the salts thereof, in particular the salts of compound (Ia) in which all the amino groups are salified, can be conveniently used in the biomedical field, in particular for the preparation of pharmaceutical compositions and membranes or devices for the treatment of biological fluids, for example dialysis membranes or devices.

Object of the present invention are therefore also pharmaceutical compositions, membranes and devices for the treatment of biological fluids which comprise compounds of formula (I).

The pharmaceutical compositions can be prepared with conventional techniques and excipients and/or carriers, for example those described in Remington's Pharmaceutical Sciences Handbook, XVII Ed. Mack Pub., N.Y., U.S.A.

The invention will be now illustrated in more detail by means of some examples.

EXAMPLES

Example 1

Preparation of Compound (Ia) and its Salt with Trifluoroacetic Acid

For further clarity, the reaction sequence is also illustrated in the Scheme following the examples. In the text, the compounds will be numbered according to the Scheme.

Starting compound p-tert-butylcalix[8]arene (II), was synthesized according to the procedure reported in the literature[14], but is also commercially available.

Step a) Synthesis of Compound (IIIa)

p-Tert-butylcalix[8]arene (II) (10 g, 7.71 mmoles) is dissolved in a round-bottom flask with condenser in a DMF/THF mixture (1:3) and placed in a warming bath at 80° C., under stirring. The mixture is added with NaH (1.850 g, 77.1 mmoles) and, after 30 min., propyl iodide (13 g, 7.52 ml, 77.1 mmoles) dissolved in 5 ml of THF, is added drop by drop. The mixture is reacted for about 12 h. Most of the solvent is distilled off under reduced pressure, then 100 ml of 0.1 N HCl is added to remove the excess of unreacted NaH; the resulting precipitate is filtered through gooch, washed with 10 ml of methanol and dried. 12 g (96% yield) of compound (IIIa) is obtained.

Step b) Synthesis of Compound (IVa)

Compound (IVa) is obtained following a procedure previously reported in the literature for the nitration of p-tert-butylcalix[4]arenes.[15]

2.5 g of compound (IIIa) is dissolved in 18 ml of $CH_2Cl_2$, thereafter 15 ml of glacial $CH_3COOH$ is added, followed by 10 ml of $HNO_3$, drop by drop. The reaction is allowed to proceed at room temperature for about 7 h, then $H_2O$ is added, the organic solvent is distilled off under reduced pressure, and the resulting yellow precipitate is filtered. Compound (IVa) is obtained in pure form by precipitation from acetone (1 g, 40% yield).

Step c) Synthesis of Compound (Va)

A catalytic amount of C/Pd and $H_2$ (2 bar) is added to 1 g of compound (IVa) dissolved in methanol/ethyl acetate (20 ml, 3:7). The mixture is left under stirring at room temperature for 24 h. The catalyst is filtered off and the solvent is evaporated off under reduced pressure to give the corresponding octaamino-octapropoxy derivative (Va) (0.85 g, yield 95%). The compound was characterized by $^1$H-NMR spectroscopy (400 MHz, $CDCl_3$, 297 K) δ 0.98 (t, J=7.3 Hz, 24H), 1.76 (q, J=6.8 Hz, 16H), 3.69 (t, J=6.5 Hz, 16H), 3. 86 (s, 16H), 6.17 (s, 16H).

Step d) Synthesis and Salification of Derivative (Ia)

Boc-Lys(Boc)-OH (418 mg, 1.2 mmoles) and 1-hydroxy-1H-benzotriazole (HOBT, 193 mg, 1.4 mmoles) are dissolved in a small round-bottom flask in 5 ml of dry DMF under stirring at room temperature. 5' N,N'-dicyclohexylcarbodiimide (DCC, 270 mg, 1.3 mmoles) is added and after further 15' the solution becomes opalescent, which indicates activation of the amino acid. The octaamino-octapropoxy derivative (Va) (130 mg, 0.1 mmoles) is added drop by drop, dissolved in 2 ml of dry DMF. The reaction is left under stirring for 3 h, then filtered and evaporated to dryness under reduced pressure. The reaction mixture is then subjected to column chromatography on silica gel at atmosphere pressure using a $CH_2Cl_2$/EtOH gradient, starting from 96:4 to 92:8. 302 mg of acylated intermediate derivative is obtained (yield 78%) which, by treatment with trifluoracetic acid for 1 h, yields the corresponding salt. The compound was characterized by means of MS, $^1H$ and $^{13}C$ NMR spectroscopy. $^1H$-NMR spectrum signals are hereinafter reported: (400 MHz, DMF $d_6$, 297 K) δ 0.78 (t, J=7.2 Hz, $CH_3$, 24H), 1.59 (m, 2×$CH_2$, 32H), 1.79 (m, $CH_2$, 16H), 2.02 (m, $CH_2$, 16H), 3.03 (t, J=6.5 Hz, $OCH_2$, 16H), 3.53 (m, $CH_2NH_3^+$, 16H), 3.98 (bs, $ArCH_2Ar$, 16H), 4.23 (bt, J=6.2 Hz, CH, 8H), 7.45 (s, ArH, 16H), 8.42 (bs, $NH_3^+$, 24H), 8.78 (bs, $NH_3^+$, 24H), 10.61 (s, NH, 8H).

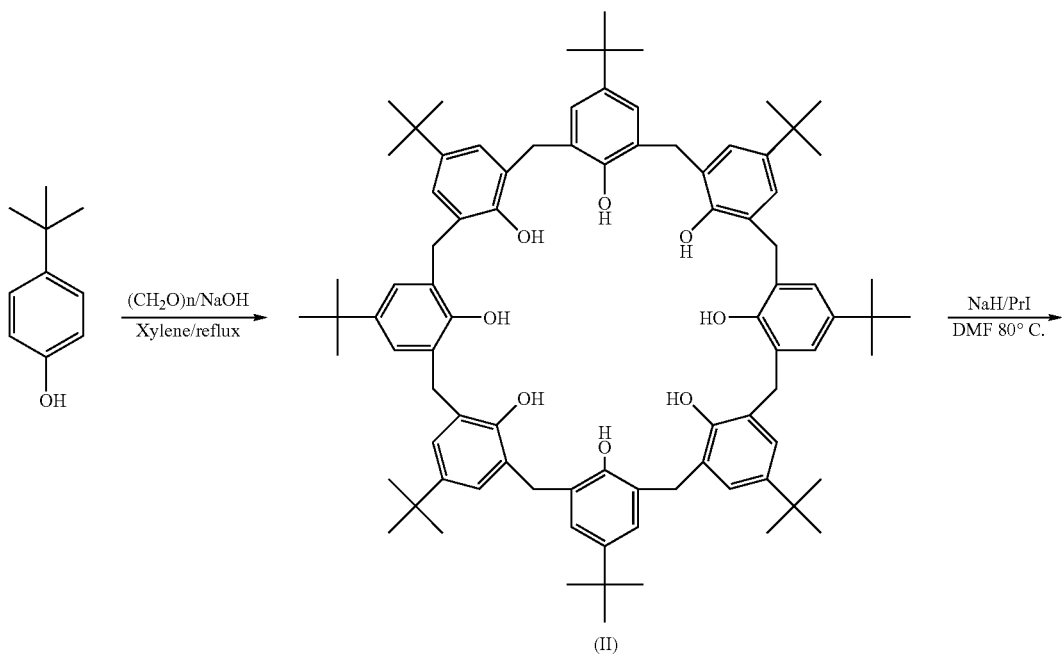

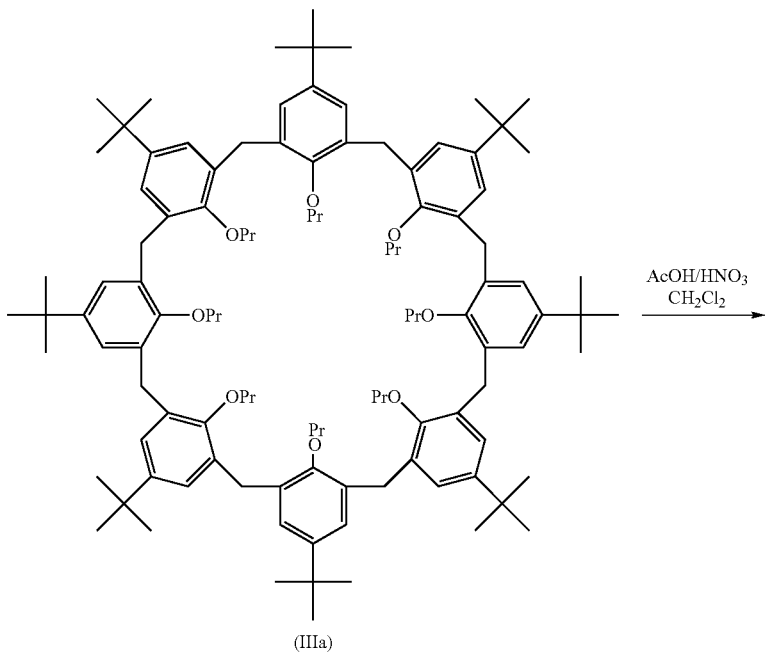

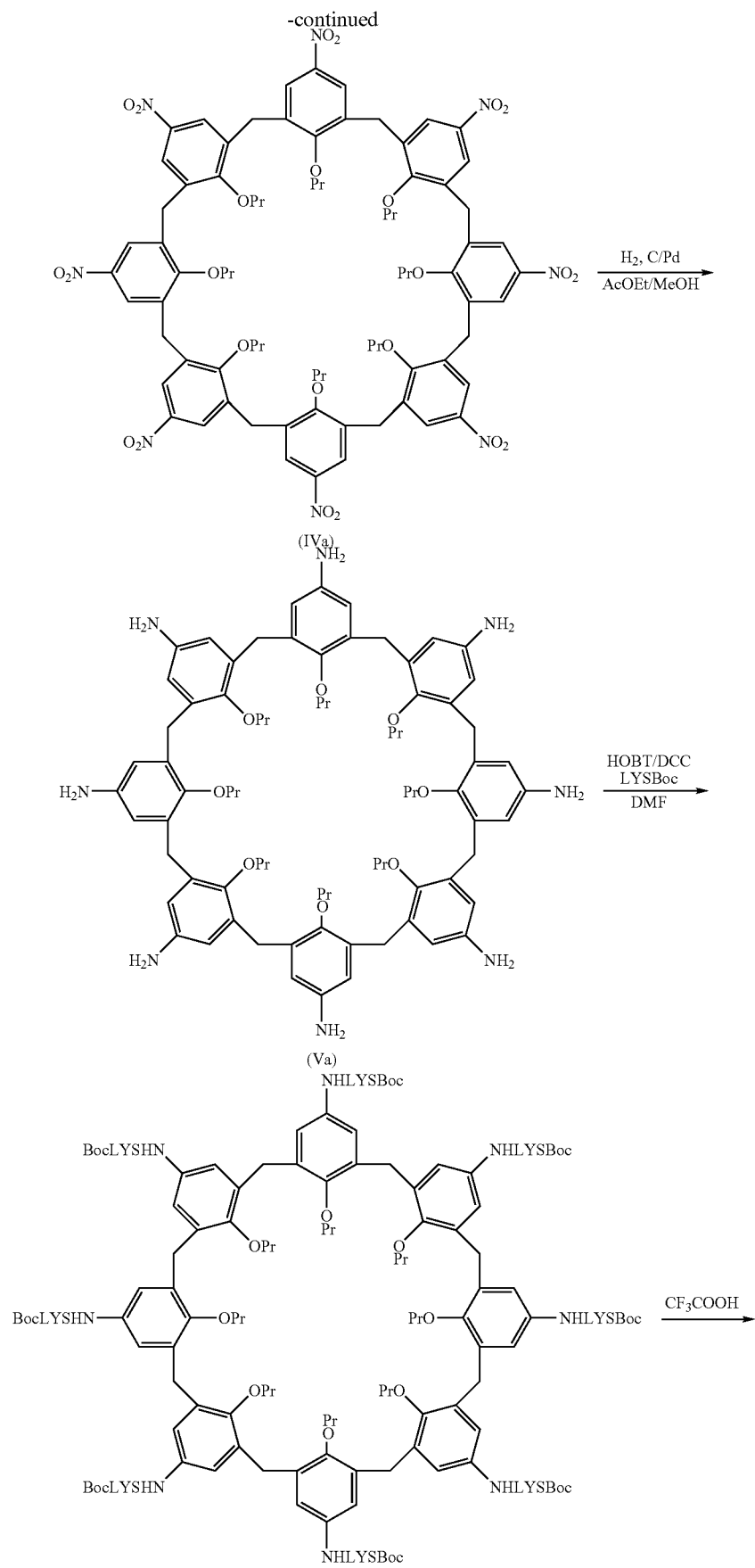

-continued

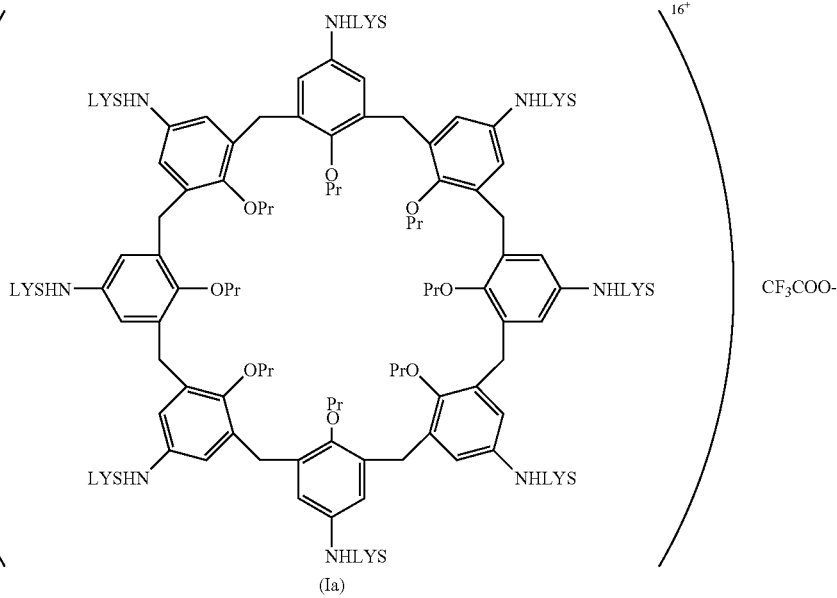

(Ia)

Example 2

Activity Assay

Due to the numerous positive charges exposed by the salt of compound (Ia), identification analysis in water in comparison with high molecular weight (about 15.000 Daltons) heparin from pig intestinal mucosa evidence immediate agglutination of the solution, with formation of an inactive complex between heparin and the synthetic receptor. Similar results were also obtained with low molecular weight (3.000 and 6.000 Daltons) heparin. In particular, using the salt of derivative (Ia), which exposes 16 positive charges in total, it was possible to quantify the activity in comparison with heparin. Using nuclear magnetic resonance spectroscopy as analysis system, in aqueous solution, 1 mg of salt neutralized 180 USP of heparin from pig intestinal mucosa, which corresponds to a double activity compared to that of protamine towards the same substrate.

LITERATURE

1. Bjork I., Lindhal U. "Mechanism of the anticoagulant action of heparin" *Mol. Cell. Biochem.* 1982, 48, 161-182.
2. Kjellen L., Lindhal U. "Proteoglycans: structure and interactions" *Ann. Rev. Biochem.* 1991, 60, 443-475.
3. Risau W. "Mechanisms of angiogenesis" *Nature* 1997, 386, 671-674.
4. Hanahan D., Folkman J. "Patterns and emerging mechanism of the angiogenic switch during tumorigenesis" *Cell* 1996, 86, 353-364.
5. Leung D. W. et al. "Vascular endothelial growth factor is a secreted angiogenic mitogen" *Science* 1989, 246, 1306-1309.
6. Soncin F. et al. "Interaction of heparin with human angiogenin" *J. Biol. Chem.* 1997, 272, 9818-9824.
7. Capila, I. et al. "Heparin-protein interactions" *Angew. Chem. Int. Ed.* 2002, 41, 390-412.
8. Porsche R., Brenner Z. R. "Allergy to protamine sulphate" *Heart & Lung* 1999, 28, 418-428.
9. Renaux, J.-L., Atti, M. "The AN69ST Dialisys Membrane. A new approach to reducing systemic heparinization" in Hemodialysis Technology. Karger: Basel, 2002, vol. 137, 111-119.
10. Hamuro, Y. et al. *Angew. Chemie Int. and. Engl.;* 1997, 36, 2680-2683.
11. Park, H. S. et al. *J. Am. Chem. Soc.* 1999, 121, 8-13.
12. Blaskovich, M. A. et al. *Nature Biotechnology,* 2000, 18, 1065-1070.
13. Reviews: Böhmer, V. Angew. Chem., Int. Ed. Engl. 1995, 34, 713. Ikeda, A.; Shinkai, S. Chem. Rev. 1997, 97, 1713. Gutsche, C. D. Calixarenes Revisited; Royal Society of Chemistry: Cambridge, 1998. Calixarenes 2001; Asfari, Z.; Böhmer, V.; Harrowfield, J.; Vicens J.; Eds.; Kluwer: Dordrecht, 2001.
14. Munch, J. H., Gutsche, C. D. *Org. Synth.* 1990, 68, 243.
15. Verboom, W. et al. *J. Org. Chem.* 1992, 57, 1313.

The invention claimed is:

1. A heparin-binding calixarene compound of formula (I):

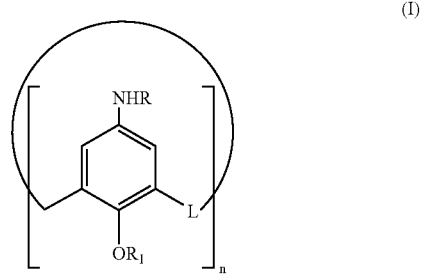

(I)

wherein:
groups R are independently an amino acid acyl residue selected from the group consisting of: lysine, β-alanine, γ-amino-butyric acid, 6-amino-hexanoic acid, 8-amino-octanoic acid, norleucine, and glycine;
$R_1$ is hydrogen, straight or branched $C_1$-$C_5$ alkyl, or benzyl;
L is $CH_2$, $CH_2OCH_2$ or S;

n is an integer ranging from 4 to 12; and salts thereof with physiologically compatible acids.

2. The heparin-binding calixarene compound according to claim 1, in which n is 8.

3. The heparin-binding calixarene compound according to claim 1, in which L is $CH_2$.

4. The heparin-binding calixarene compound according to claim 1, in which $R_1$ is propyl.

5. The heparin-binding calixarene compound as claimed in claim 1, wherein:

groups R are independently the acyl residue of an amino acid selected from the group consisting of: lysine, β-alanine, γ-amino-butyric acid, 6-amino-hexanoic acid, 8-amino-octanoic acid, norleucine and glycine;

$R_1$ is propyl;

L is $CH_2$; and n is 8.

6. The heparin-binding calixarene compound as claimed in claim 5, in which the groups R are lysine acyl residues.

7. A pharmaceutical composition comprising the heparin-binding calixarene compound of claim 1 in admixture with suitable excipients and/or carriers.

8. A method of preparing a pharmaceutical composition, said method comprising mixing the heparin-binding calixarene compound of claim 1 with a pharmaceutically acceptable excipient and/or carrier.

9. A method of preparing a dialysis membrane, said method comprising contacting said dialysis membrane with the heparin-binding calixarene compound of claim 1.

10. A method of treating biological fluids, said method comprising contacting the heparin-binding calixarene compound of claim 1 with a biological fluid in need of treatment thereof.

11. A method of preparing a pharmaceutical composition, said method comprising mixing a pharmaceutically acceptable excipient and/or carrier with a heparin-binding calixarene compound of formula (I):

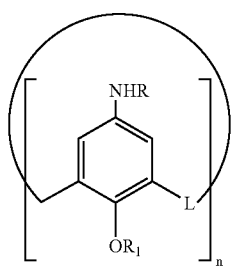

(I)

wherein:

groups R are independently hydrogen or an amino acid acyl residue selected from the group consisting of: lysine, β-alanine, γ-amino-butyric acid, 6-amino-hexanoic acid, 8-amino-octanoic acid, norleucine, and glycine;

$R_1$ is hydrogen, straight or branched $C_1$-$C_5$ alkyl, or benzyl;

L is $CH_2$, $CH_2OCH_2$ or S;

n is an integer ranging from 4 to 12; or salts thereof with physiologically compatible acids.

12. A method of preparing a dialysis membrane, said method comprising contacting said dialysis membrane with a heparin-binding calixarene compound of formula (I):

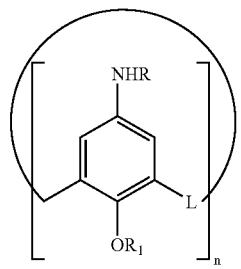

(I)

wherein:

groups R are independently hydrogen or an amino acid acyl residue selected from the group consisting of: lysine, β-alanine, γ-amino-butyric acid, 6amino-hexanoic acid, 8-amino-octanoic acid, norleucine, and glycine;

$R_1$ is hydrogen, straight or branched $C_1$-$C_5$ alkyl, or benzyl;

L is $CH_2$, $CH_2OCH_2$ or S;

n is an integer ranging from 4 to 12; or salts thereof with physiologically compatible acids.

13. A method of treating biological fluids, said method comprising contacting a biological fluid with a heparin-binding calixarene compound of formula (I):

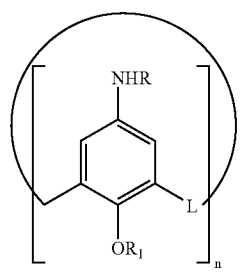

(I)

wherein:

groups R are independently hydrogen or an amino acid acyl residue selected from the group consisting of: lysine, β-alanine, γ-amino-butyric acid , 6-amino-hexanoic acid, 8-amino-octanoic acid, norleucine, and glycine;

$R_1$ is hydrogen, straight or branched $C_1$-$C_5$ alkyl, or benzyl;

L is $CH_2$, $CH_2OCH_2$ or S;

n is an integer ranging from 4 to 12; or salts thereof with physiologically compatible acids.

\* \* \* \* \*